United States Patent [19]
Liao et al.

[11] Patent Number: 5,647,979
[45] Date of Patent: Jul. 15, 1997

[54] ONE-STEP PREPARATION OF SEPARATION MEDIA FOR REVERSED-PHASE CHROMATOGRAPHY

[75] Inventors: Jia-Li Liao, San Pablo, Calif.; Stellan Hjertén, Upsala, Sweden

[73] Assignee: Bio-Rad Laboratories, Inc., Hercules, Calif.

[21] Appl. No.: 666,061

[22] Filed: Jun. 14, 1996

[51] Int. Cl.$^6$ .................................... B01D 15/08
[52] U.S. Cl. .................... 210/198.2; 210/502.1; 210/635; 210/656; 95/88; 96/101; 502/439
[58] Field of Search ..................... 210/635, 656, 210/198.2, 502.1; 95/88; 96/101; 422/70; 436/161; 502/439

[56] References Cited

U.S. PATENT DOCUMENTS

| | | | |
|---|---|---|---|
| 4,135,892 | 1/1979 | Coupek | 55/67 |
| 4,281,233 | 7/1981 | Coupek | 210/198.2 |
| 4,497,710 | 2/1985 | Wagu | 210/635 |
| 4,696,745 | 9/1987 | Itagaki | 210/502.1 |
| 5,334,310 | 8/1994 | Frechet | 210/198.2 |
| 5,522,994 | 6/1996 | Frechet | 210/198.2 |

FOREIGN PATENT DOCUMENTS

| | | | |
|---|---|---|---|
| 0 407 560 B1 | 6/1995 | European Pat. Off. | 210/198.2 |
| 6803739 | 9/1969 | Netherlands | 210/198.2 |
| WO9007965 | 7/1990 | WIPO | 210/198.2 |

*Primary Examiner*—Ernest G. Therkorn
*Attorney, Agent, or Firm*—Townsend and Townsend and Crew LLP

[57] ABSTRACT

A separation medium for reversed-phase chromatography is prepared by polymerizing an aqueous vinyl monomer mixture to which a hydrophobic alkyl methacrylate with 3 or more carbon atoms in the alkyl group and a detergent have been added. The further inclusion of a vinyl monomer with a charged group in the reaction mixture produces a separation medium useful for reversed-phase electrochromatography. Performance of the polymerization in a capillary produces a continuous bed inside the capillary. An alternative for non-capillary separations, such as those conducted in larger diameter tubing, is the preparation of the medium in a vessel outside the tubing, followed by granulation of the polymer and placement of the granules in the tubing.

31 Claims, 4 Drawing Sheets

ONE-STEP PREPARATION OF SEPARATION MEDIA FOR REVERSED-PHASE CHROMATOGRAPHY

This invention relates to reversed-phase chromatography, and in particular to the preparation of chromatographic media for the various forms of reversed-phase chromatography.

BACKGROUND OF THE INVENTION

Reversed-phase chromatography requires the use of a separation medium that contains hydrophobic alkyl groups as contact sites on the medium surface. The medium itself is a polymer generally formed by polymerization in an aqueous solution, and the inclusion of the hydrophobic alkyl groups requires a further reaction in a nonaqueous medium on the surface of the polymer itself after the polymer has been formed. In large-scale production or in laboratory situations where a large number of analyses or columns are needed, the time required for a second reaction can affect cost and efficiency. Furthermore, when the polymer is porous, penetration of the pores becomes a factor in both the rate of reaction and the uniformity of distribution of the hydrophobic groups on the polymer surface.

Reversed-phase chromatography can be performed in capillaries as well as relatively large-diameter tubing. The use of a capillary permits separations to be performed at high voltage with the rapid dissipation of heat to avoid excessive joule heating. Further advantages are the use of very small amounts of sample, and the completion of an analysis in a relatively short period of time. A reversed-phase separation however requires that the capillary be packed with solid phase such as beads, which is difficult to do in a capillary, particularly in a manner that will result in a uniform packing density. Another difficulty in the use of a packed capillary is that a supporting frit is generally required at the capillary outlet to hold the beads in place. Preparation of the frit is not a simple task, and the frit often generates air bubbles during the separation. For these reasons, capillaries are not widely used for reversed-phase chromatography.

These disadvantages are eliminated by the formation of a continuous bed in the capillary, i.e., a monolithic porous polymer used in place of the beads, the polymer having been formed by polymerization in the capillary itself, spanning the entire cross section of the capillary and bonded to the capillary wall. A description of this type of bed is found in granted European Patent Specification No. 0 407 560 of Bio-Rad Laboratories, Inc., and its United States counterpart, pending application Ser. No. 08/400,419, filed Mar. 2, 1995. The disclosures of both of these documents are incorporated herein by reference.

Like polymeric separation media in general, however, the formation of a continuous porous polymer bed is performed with an aqueous solution, and the resulting bed is at least primarily hydrophilic. The subsequent reaction to place hydrophobic groups on the polymer surface must be performed inside the capillary, and here again, the need for two reactions adds to the cost of the column.

SUMMARY OF THE INVENTION

It has now been discovered that a separation medium for reversed-phase chromatography can be prepared in a one-step reaction by polymerizing an aqueous vinyl monomer mixture that includes both a hydrophobic alkyl methacrylate where the alkyl group has 3 or more carbon atoms, and a detergent. The remaining components of the monomer mixture include either a vinyl monomer, an acrylic monomer or a methacrylic monomer, plus a crosslinking agent, all hydrophilic prior to polymerization, plus initiators or catalysts as necessary. The detergent serves to incorporate the hydrophobic non-water-soluble alkyl methacrylate into the aqueous reaction mixture to provide full reactive access between the alkyl methacrylate and the hydrophilic components of the mixture, and thereby incorporate the hydrophobic alkyl group homogeneously into the resulting polymer. The medium is thus formed by a one-step reaction, all reactants being combined in a single reaction mixture prior to the polymerization.

The invention is useful for the preparation of a granulated separation medium which once formed can be placed inside separation vessels of any shape, size or configuration, and also for the preparation of a continuous bed filling the interior of the vessel. One area of particular interest is the formation of a continuous bed in a capillary, where the reaction mixture immediately after formation is drawn into the capillary so that the polymerization occurs in the capillary interior. The capillary is thus ready for use in a considerably shorter period of time. The invention is adaptable for electrochromatography, either in a capillary or otherwise, by the further inclusion in the polymerization mixture of a vinyl monomer with a charged group.

These and other objects, features and advantages of the invention will be apparent from the description that follows.

DETAILED DESCRIPTION OF THE INVENTION AND PREFERRED EMBODIMENTS

Figure 1:
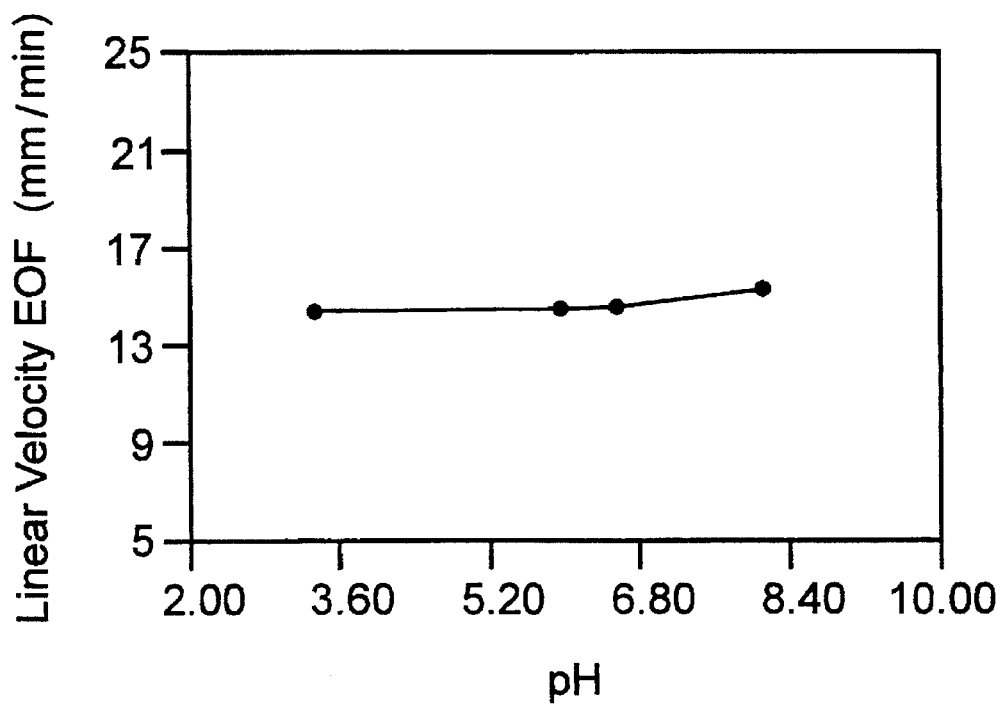
FIG. 1 is a plot of bulk flow rate caused by electroosmotic flow vs. the pH of the running buffer, using a continuous bed prepared in accordance with this invention.

The hydrophilic monomer system to which the charged monomers and hydrophobic monomers are added consists of monomers that are sufficiently hydrophilic to form aqueous solutions, with solubilities of at least about 10%. The monomers of interest are vinyl, acrylic and methacrylic monomers. Specific examples are vinyl acetate, vinyl propylamine, acrylamide, methacrylamide, glycidyl methacrylate, and glycidyl acrylate.

Crosslinking agents suitable for use in the present invention include any bifunctional species capable of reacting with the monomer in a crosslinking manner. For polyacrylamides and polymers of other forms of acrylic acid, examples of suitable crosslinking agents are bisacrylamides, diacrylates, and a wide range of terminal dienes. Specific examples are dihydroxyethylenebisacrylamide, diallyltartardiamide, triallyl citric triamide, ethylene diacrylate, bisacrylylcystamine, N,N'-methylenebisacrylamide and piperazine diacrylamide.

The hydrophobic alkyl methacrylate is an alkyl ester of methacrylic acid, the alkyl of the alcohol moiety of the ester being any alkyl group that will serve as a hydrophobic group for reversed-phase chromatography. Preferred alkyls are those having 3 to 30 carbon atoms, and further preferred are those that are saturated, with at least three carbon atoms arranged in a linear chain. Still further preferred are those that contain 6 to 30 carbon atoms, still further 10 to 30 carbon atoms, and still further 12 to 20 carbon atoms, all saturated and in an unbranched chain. For hydrophobic interaction chromatography, n-butyl methacrylate is particularly preferred, and for other types of reversed-phase chromatography, stearyl ($C_{18}$) methacrylate is particularly preferred. Other specific examples are n-octyl ($C_8$), capric ($C_{10}$), lauryl ($C_{12}$), myristyl ($C_{14}$), cetyl ($C_{16}$), arachidyl ($C_{20}$), and docosanyl ($C_{22}$) methacrylates.

The detergent can be any of the wide variety of detergents known to those skilled in the art. Preferred detergents are nonionic detergents, and further preferred detergents are those having a hydrophile-lipophile balance within the range of about 10 to about 15, particularly from about 12 to about 14. Ethoxylated alkylphenols are one class of nonionic detergents that can be used effectively in this invention. Further examples are ethoxylated glycerides and glyceride derivatives, alkyl polysaccharide ethers, alkyl ethers of polyethylene glycol, and sorbitan monolaurates. Other examples will be readily apparent to those skilled in the art.

When charged monomers are included in the reaction mixture to achieve media suitable for electrochromatography, the charged groups on these monomers can be either positively charged or negatively charged. Each charged monomer will further contain a terminal vinyl group to permit incorporation into the polymer chain. Examples of monomers with positively charged groups are dimethylaminoethyl methacrylate, 2-trimethylammoniomethyl methacrylate chloride, diethylaminoethyl acrylate, and dimethyl diallyl ammonium chloride. Examples of monomers with negatively charged groups are vinyl sulfonic acid, acrylic acid, methacrylic acid, 2-acrylamidoglycolic acid, and 2-acrylamido-2-methyl-1-propanesulfonic acid. Many other suitable examples of both types are well known and readily available from commercial suppliers.

The quantities of hydrophilic uncharged monomer, crosslinker, charged monomer and hydrophobic monomer can vary considerably within the scope of the invention. For best results, however, certain ranges are preferred. The total of the concentrations of the monomers and crosslinker, whether or not the monomers include a charged monomer for electrochromatography, are preferably within the range of about 2% to about 50% of the aqueous reaction mixture, on a weight basis. More preferably, the range of total concentrations is from about 10% to about 30%, although in certain cases the total is preferably within a range of about 2% to about 5%. The mole fraction of the crosslinking agent relative to the monomer combination (with or without the charged monomer) is preferably within the range of about 0.10 to about 0.70. More preferably, this mole fraction is within the range of about 0.2 to about 0.4, although in certain cases the more preferred range is about 0.4 to about 0.6.

A preferred range for the mole fraction of the charged monomer relative to the total monomers plus crosslinker is about 0.03 to about 3.0, and a more preferred range is about 0.1 to about 1.0. A preferred range for the hydrophobic alkyl methacrylate monomer relative to the total monomers plus crosslinker is about 0.003 to about 0.3, and a more preferred range is about 0.01 to about 0.10. A preferred range for the mole ratio of detergent relative to the hydrophobic alkyl methacrylate is about 0.03 to about 3.0, and a more preferred range is from about 0.1 to about 1.0.

The remainder of the reaction mixture is an aqueous solution, as conventionally used for polymerization reactions of this type. The solution will generally contain additional components as needed for the polymerization to occur, typically initiators, catalysts or both. The selection of these components will be readily apparent to those skilled in the art.

When the reaction is performed in a capillary to form a continuous bed, the size of the capillary is not critical and may vary. Preferred capillaries are those having internal diameters of less than about 500 microns, and most preferably about 10 microns to about 300 microns. For silica capillaries, it is frequently beneficial to coat the capillary wall prior to drawing the reaction mixture into the capillary. An appropriate coating will be one that covalently binds reactive groups to the capillary wall which will then bond to the polymer during the polymerization reaction. For silica capillaries, the coating can be a bifunctional compound containing one functional group that binds to free hydroxyl groups on the silica surface and another that reacts with the monomers in the polymerization reaction occurring in the aqueous reaction mixture. Examples of such bifunctional compounds are γ-methacryloxypropyltrimethylsilane, vinyltriacetoxysilane, vinyltri(β-methoxyethoxy)silane, vinyltrichlorosilane, and methylvinyldichlorosilane.

Once the polymerization reaction is complete, nonreacted materials such as the detergent and the polymerization initiators are removed from the bed by flushing the capillary with deionized water or other appropriate liquid, and equilibrating the column with the mobile phase to be used in the separation.

The following examples are offered for illustration only.

EXAMPLE 1

This example compares electroosmotic flow rates with mobile phases of differing pH, to verify that the electroosmotic flow originates with the charged groups on the continuous bed polymer, rather than the mobile phase itself.

A monomer mixture was prepared by combining the following in 1 mL of 0.015 M Tris-HCl at pH 8.5:

0.12 g piperazine diacrylamide 0.075 g methacrylamide 0.065 g ammonium sulfate

150 μL vinyl sulfonic acid

To 400 μL of this solution were added 50 mg of stearylmethacrylate, melted at 37° C., and 15 μL of TRITON® X-100, a nonionic ethoxylated alkylphenol detergent identified as octylphenoxypolyethoxyethanol having a HLB of 13.5, a product of Union Carbide Corporation, Danbury, Conn., USA. The resulting mixture was heated in a water bath to the cloud point of the detergent and mixed, followed by the addition of ammonium persulfate (5μL of a 10 weight percent aqueous solution) and 4 μL of N,N,N',N'-tetramethylethylenediamine. The mixture was then immediately drawn into fused silica capillary tubing precoated with γ-methacryloxypropyltrimethoxysilane, the capillary measuring 100 microns internal diameter and having an effective length of 160 ram. Polymerization was allowed to proceed overnight. The capillary was then rinsed with deionized water, acetonitrile, and finally with the mobile phase, which was 60 volume percent acetonitrile in 4 mM sodium phosphate at various pH values, as indicated below.

A sample consisting of polycyclic aromatic hydrocarbons was prepared by dissolving naphthalene, 2-methyl naphthalene, fluorene, phenanthrene and anthracene, dissolved in 4 mM sodium phosphate, pH 7.4, containing 60% (by volume) acetonitrile. A quantity of vitamin $B_{12}$ (cyanocobalamin) was included in the sample to provide a measure of the migration time. The sample was injected into the column by electrophoretic means at a voltage of 1,000 V for 2 seconds. The separation was then performed with an applied voltage of 3.0 kV. On-line detection was performed through the capillary itself, by absorption of ultraviolet light.

Four runs were performed, differing only in the pH of the mobile phase, using pH's of 3.4, 6.0, 6.6 and 8.2. Using the $B_{12}$ as a marker, the electroosmotic flow was determined in millimeters per minute as a function of the mobile phase pH, and the results are plotted in FIG. 1. The plot shows that the velocity of the electroosmotic flow is independent of the pH of the mobile phase. This indicates that the electroosmotic flow originates from the sulfonic acid ligands in the continuous bed. The column thus offers the advantage of allowing the separation to be performed at a pH selected to achieve optimum separation for any given mixture of solutes. The ability to select a pH that is optimal for a particular solute mixture is not available in silica beds where the osmotic flow varies with the pH.

EXAMPLE 2

This example compares the effect of acetonitrile content in the mobile phase on the capacity factor of each solute.

Figure 2:
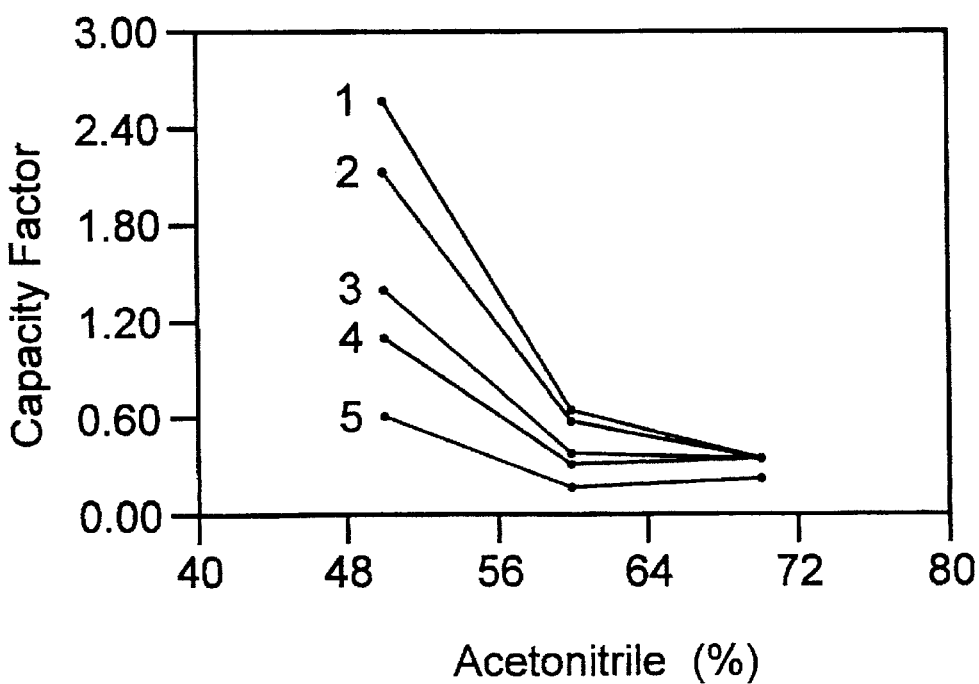
FIG. 2 is a plot of the capacity factors of the solutes in a sample mixture vs. the acetonitrile content of the running buffer when the sample mixture is separated in a continuous bed prepared in accordance with this invention.

A series of separations were performed using a column prepared as described in Example 1 at the same voltage, and a sample identical to that of Example 1. Three separations were performed, using different mobile phases—50%, 60% and 70 % (by volume) acetonitrile, all in 4 mM sodium phosphate at pH 7.0. The capacity factor k' for each solute, defined as the ratio of the amount of solute present in the stationary phase to that in the mobile phase, and calculated as:

$$k' = \frac{t_R - t_o}{t_o}$$

where $t_R$ is the retention time of the solute and $t_o$ is the elution time of an unrestrained component ($B_2$), was determined and is plotted in FIG. 2. In this and all subsequent examples, naphthalene is designated by the numeral 1, 2-methyl naphthalene by the numeral 2, fluorene by the numeral 3, phenanthrene by the numeral 4, and anthracene by the numeral 5.

The results show that a decrease in the concentration of acetonitrile below 60% by weight produces an increase in the capacity factor of each solute. This is consistent with the interaction between acetonitrile and hydrophobic groups in the stationary phase: lowering the acetonitrile content produces greater interaction between the non-polar solutes and the stationary phase. The greater interaction improves resolution but lengthens the migration time.

EXAMPLE 3

This example illustrates how improved peak resolution can be achieved by narrowing the starting zone of solutes. The starting zone was narrowed by increasing the net velocity of the rear of the applied sample zone relative to that of the front of the zone. This was achieved by raising the concentration of acetonitrile at the rear of the applied sample zone in a stepwise increase from 50% to 70% (by volume). This caused both a narrowing of the starting zone and a gradient elution due to the gradual equilibration of the column from 50% to 70% acetonitrile.

Two separations were performed—one with the zone narrowing and gradient elution, and a control run with neither. The capillary in both cases had internal diameter of 75 microns and an effective length of 160 ram, and in both cases the same sample described in Example 1 (without the $B_{12}$) was used with an applied voltage of 3.0 kV.

Figure 3A:
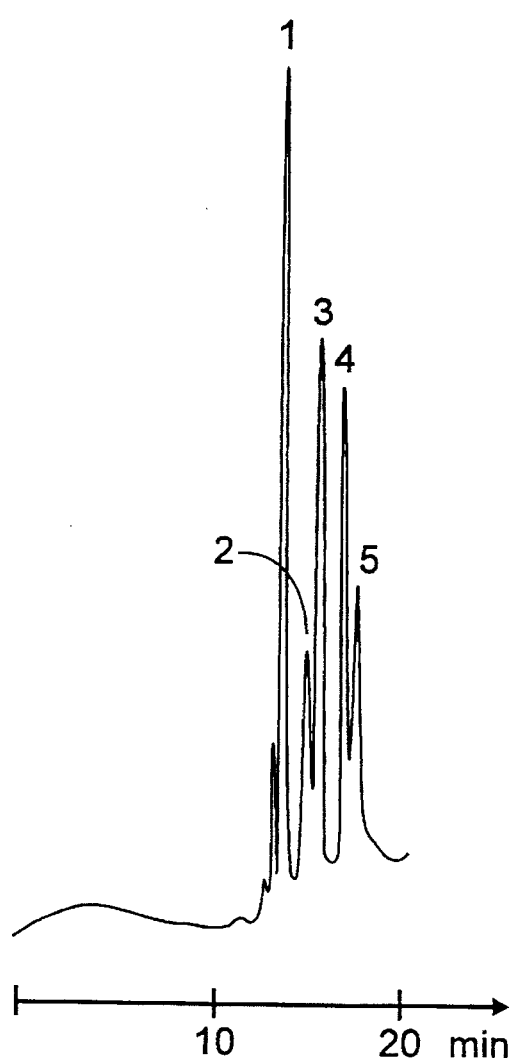
FIGS. 3a and 3b are chromatograms of a sample mixture obtained on a continuous bed prepared in accordance with this invention, the separation performed using a running buffer with a constant acetonitrile content (FIG. 3a) and a running buffer with a stepwise increase in the acetonitrile content (FIG. 3b).
Figure 3B:
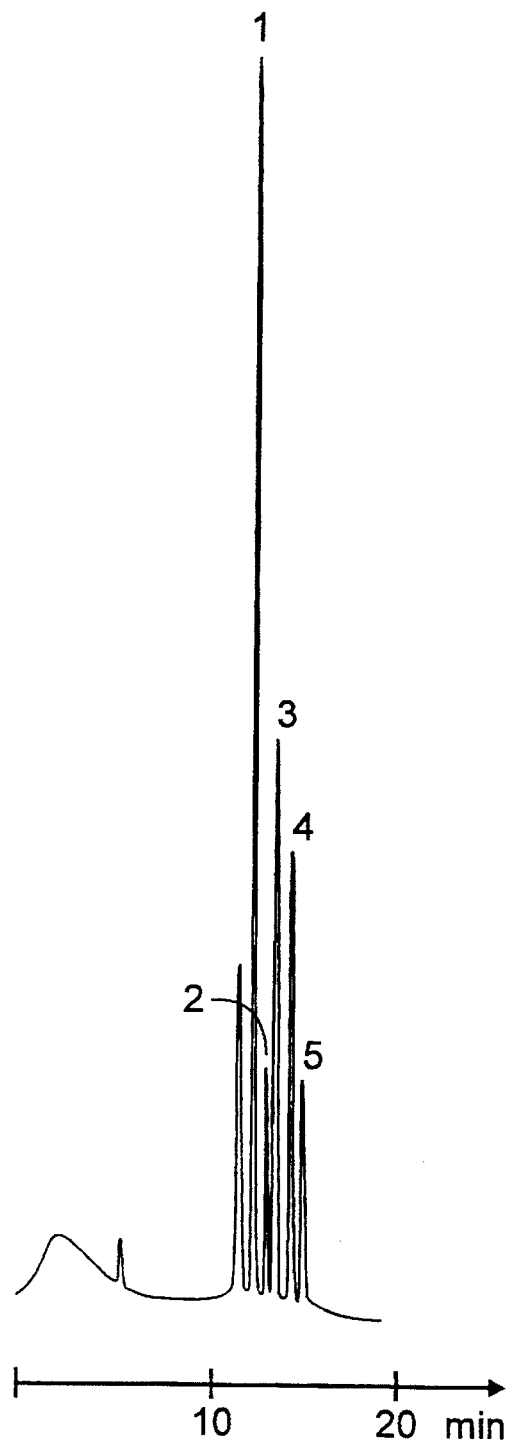

In the control run, the running buffer contained 60% acetonitrile (by volume) in 4 mM phosphate buffer at pH 7.4. The resulting chromatogram is shown in FIG. 3a, where the peaks are numbered as indicated in Example 2. In the test run, the mobile phase at the start of the separation was 50% acetonitrile in 4 mM phosphate buffer at pH 7.4, and was replaced after six minutes with 70% acetonitrile in 4 mM phosphate buffer at pH 7.4. The chromatogram is shown in FIG. 3b. A comparison of the two chromatograms shows that the combination of zone sharpening and gradient elution in FIG. 3a results in peaks of lesser width and consequently greater resolution compared to FIG. 3b.

EXAMPLE 4

This example illustrates how resolution can be improved by the inclusion of sodium dodecyl sulfate (SDS) in the mobile phase, at a concentration below its critical micelle concentration. The SDS was included in the expectation that the hydrophobic dodecyl group on the SDS molecule would interact with the stationary $C_{18}$ group on the continuous bed, increasing both the ligand density and charge on the bed, to result in an increase in the partition of the solutes and consequently an improvement in the resolution.

A column prepared as described in Example 1 was used (except with an effective length of 100 mm rather than 160 ram), with the same sample (without $B_{12}$), mobile phase, and applied voltage. One separation was performed in this manner, and a parallel separation was performed with the additional inclusion of 1.0 mM SDS in the mobile phase.

Figure 4A:
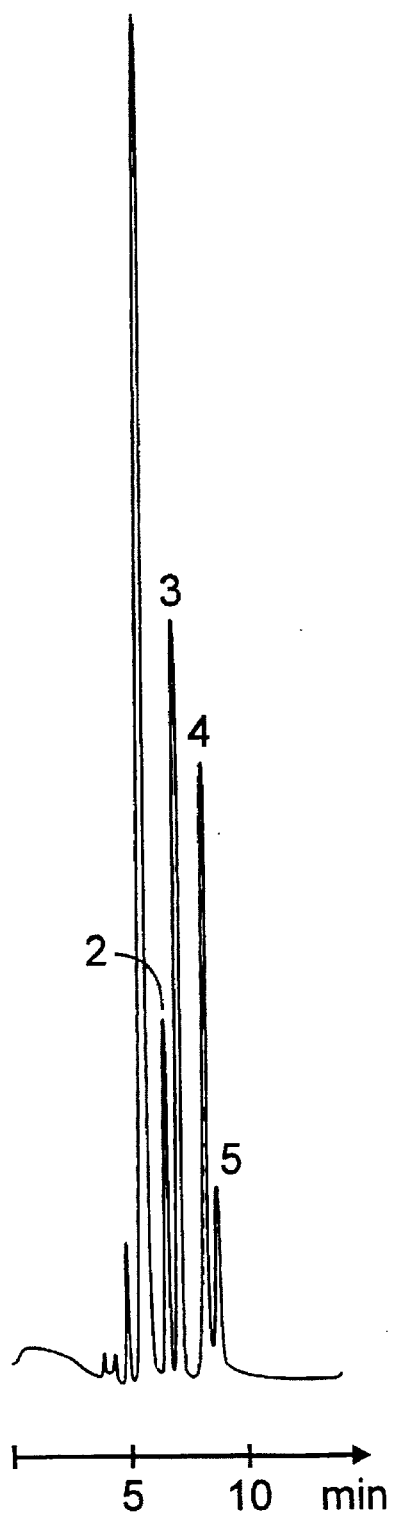
FIGS. 4a and 4b are chromatograms of a sample mixture obtained on a continuous bed prepared in accordance with this invention, using running buffers both with (FIG. 4a) and without (FIG. 4b) sodium dodecyl sulfate.
Figure 4B:
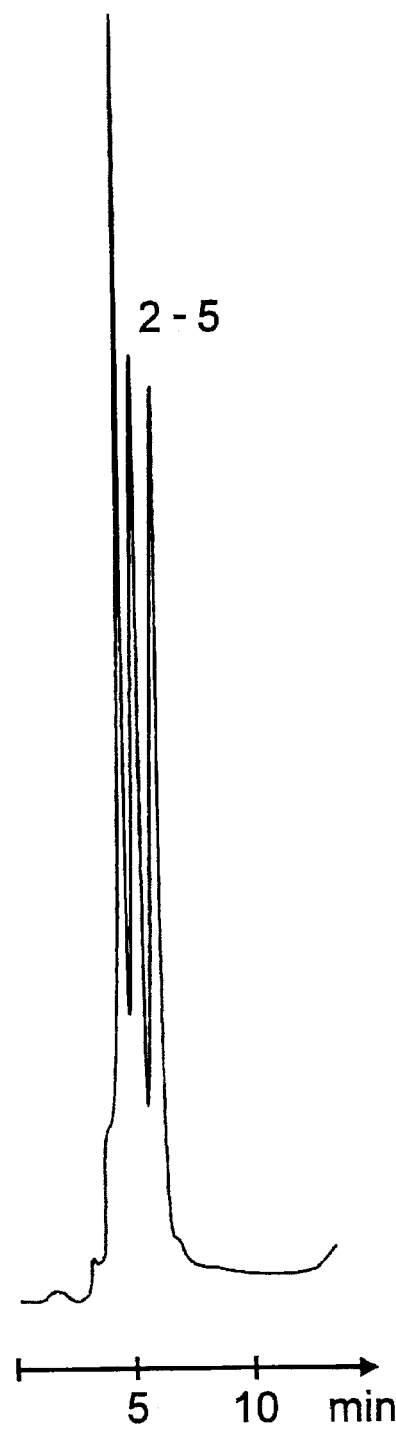

The chromatogram obtained with SDS is shown in FIG. 4a, while the chromatogram obtained without SDS is shown in FIG. 4b. Comparison indicates that the presence of SDS improved resolution so much that a baseline separation was achieved on a column only 100 mm in effective length.

EXAMPLE 5

This example illustrates the use of a particularly narrow capillary with an internal diameter of 25 microns, and a higher field strength at 10.0 kV, permitted by the greater dissipation of joule heating due to the narrow capillary. The capillary had an effective length of 175 min. All other conditions were the same as those described in Example 1 (without $B_{12}$).

Figure 5:
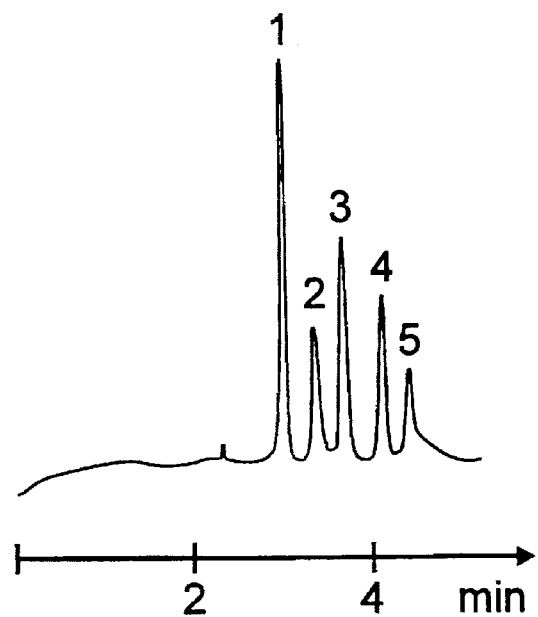
FIG. 5 is a chromatogram obtained under conditions similar to those of the preceding Figures, but using a capillary having an internal diameter that is either one-fourth or one-third the size of the capillaries used in the preceding Figures.

The results are shown in the chromatogram of FIG. 5. The chromatogram shows that the analysis time was reduced from about 20 minutes to about 5 minutes, when compared to the analysis shown in FIG. 3a where the conditions were identical except for the capillary size, with no increase in thermal broadening.

EXAMPLE 6

This example illustrates the use of a continuous bed in which the alkyl functional groups are short (n-butyl) carbon chains.

A monomer mixture identical to that of Example 1 was prepared, except that 20 μL of n-butylmethacrylate was used in place of the stearylmethacrylate. The mixture was polymerized in a capillary in the same manner described in Example 1, except that the capillary was 75 microns inner diameter. The same sample (without $B_{12}$) was used, as were the same running buffer and applied voltage.

Figure 6:
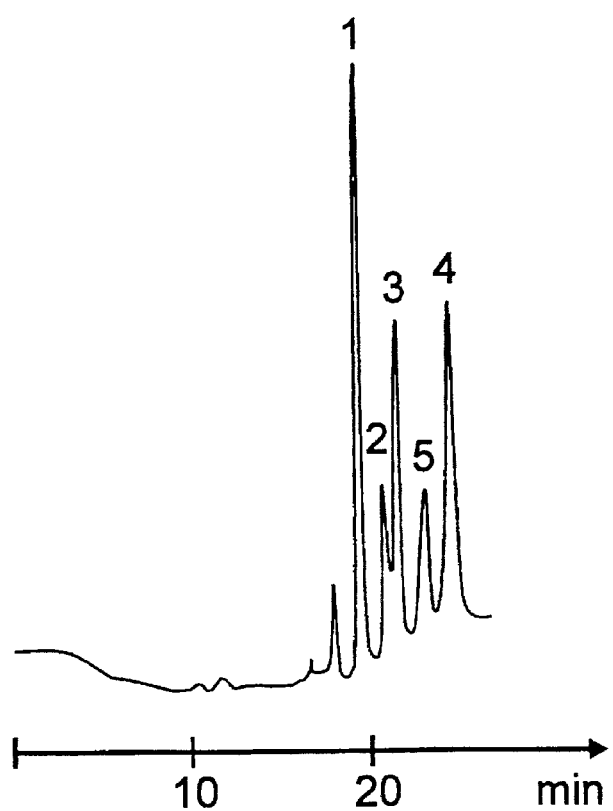
FIG. 6 is a chromatogram obtained on a different continuous bed in accordance with this invention.

The separation resulted in the chromatogram shown in FIG. 6. Comparing this chromatogram with those of 3a, 3b, 4a, 4b, and 5 shows that the peak resolution is approximately the same, but the order of elution between naphthalene and 2-methyl naphthalene is reversed.

The foregoing is offered primarily for purposes of illustration. It will be readily apparent to those skilled in the art that the materials, proportions, procedural steps and other parameters of the process described herein may be further modified or substituted in various ways without departing from the spirit and scope of the invention.

We claim:

1. A process for the preparation of a separation medium for continuous bed reversed-phase chromatography, comprising:
   (a) forming a mixture comprising the following components:
      (i) a water-soluble monomer selected from the group consisting of
      vinyl, acrylic and methacrylic monomers,
      (ii) a crosslinking agent,
      (iii) an alkyl methacrylate, the alkyl group having 3 to 30 carbon atoms, and
      (iv) a detergent,
      in an aqueous medium; and
   (b) polymerizing components (i), (ii) and (iii) in said mixture in a one-step reaction.

2. A process in accordance with claim 1 in which the sum of the weight percents of components (i), (ii) and (iii) in said mixture is from about 2% to about 50%, and the mole fraction of said crosslinking agent relative to the sum of components (i), (ii) and (iii) is from about 0.10 to about 0.70.

3. A process in accordance with claim 1 in which said alkyl methacrylate is present at a mole fraction of from about 0.003 to about 0.300 relative to the total of components (i), (ii) and (iii).

4. A process in accordance with claim 1 in which said alkyl methacrylate is present at a mole fraction of from about 0.01 to about 0.10 relative to the total of components (i), (ii) and (iii).

5. A process in accordance with claim 1 in which said detergent is present at a mole ratio of from about 0.03 to about 3.0 relative to said alkyl methacrylate.

6. A process in accordance with claim 1 in which said detergent is present at a mole ratio of from about 0.1 to about 1.0 relative to said alkyl methacrylate.

7. A process in accordance with claim 1 in which said detergent is a nonionic detergent.

8. A process in accordance with claim 1 in which said detergent is a detergent having a hydrophile-lipophile balance of from about 10 to about 15.

9. A process in accordance with claim 1 in which said detergent is a detergent having a hydrophile-lipophile balance of from about 12 to about 14.

10. A process in accordance with claim 1 in which said detergent is an ethoxylated alkylphenol.

11. A process in accordance with claim 1 in which said alkyl group of said alkyl methacrylate has from 10 to 30 carbon atoms.

12. A process in accordance with claim 1 in which said alkyl group of said alkyl methacrylate has from 12 to 20 carbon atoms.

13. A process in accordance with claim 1 in which said alkyl methacrylate is n-butyl methacrylate.

14. A process in accordance with claim 1 in which said alkyl methacrylate is stearyl methacrylate.

15. A process in accordance with claim 1 further comprising drawing said mixture into a capillary prior to step (b), and in which step (b) is performed inside said capillary.

16. A process for the preparation of a separation medium for continuous bed reversed-phase electrochromatography, comprising:
   (a) forming a mixture comprising the following components:
      (i) a water-soluble monomer selected from the group consisting of vinyl, acrylic and methacrylic monomers,
      (ii) a crosslinking agent,
      (iii) a water-soluble monomer having a terminal vinyl group and a charged group,
      (iv) an alkyl methacrylate, the alkyl group having 3 to 30 carbon atoms, and
      (v) a detergent,
      in an aqueous medium; and
   (b) polymerizing components (i), (ii), (iii) and (iv) in said mixture in a one-step reaction.

17. A process in accordance with claim 16 in which component (iii) is a member selected from the group consisting of vinyl sulfonic acid, acrylic acid, methacrylic acid, 2-acrylamidoglycolic acid, and 2-acrylamido-2-methyl-1-propanesulfonic acid.

18. A process in accordance with claim 16 in which component (iii) is present at a mole fraction of from about 0.03 to about 3.0 relative to the total of components (i), (ii), (iii) and (iv).

19. A process in accordance with claim 16 in which component (iii) is present at a mole fraction of from about 0.1 to about 1.0 relative to the total of components (i), (ii), (iii) and (iv).

20. A process in accordance with claim 16 in which component (iii) is a member selected from the group consisting of dimethylaminoethyl methacrylate, 2-trimethylammoniomethyl methacrylate chloride, diethylaminoethyl acrylate, and dimethyl diallyl ammonium chloride.

21. A process in accordance with claim 16 in which said alkyl methacrylate is present at a mole fraction of from about 0.01 to about 0.10 relative to the total of components (i), (ii), (iii) and (iv).

22. A process in accordance with claim 16 in which said detergent is present at a mole ratio of from about 0.1 to about 1.0 relative to said alkyl methacrylate.

23. A process in accordance with claim 16 in which said detergent is a detergent having a hydrophile-lipophile balance of from about 12 to about 14.

24. A process in accordance with claim 16 in which said detergent is an ethoxylated alkylphenol.

25. A process in accordance with claim 16 in which said alkyl group of said alkyl methacrylate has from 12 to 20 carbon atoms.

26. A process in accordance with claim 16 in which said alkyl methacrylate is n-butyl methacrylate.

27. A process in accordance with claim 16 in which said alkyl methacrylate is stearyl methacrylate.

28. A process in accordance with claim 16 in which component (i) is a member selected from the group consisting of acrylamide and methacrylamide, and component (ii) is a member selected from the group consisting of N,N'-methylenebisacrylamide and piperazine bisacrylamide.

29. A process in accordance with claim 16 in which component (i) is methacrylamide, component (ii) is piperazine bisacrylamide, component (iii) is vinyl sulfonic acid, and component (iv) is n-butyl methacrylate.

30. A process in accordance with claim 16 in which component (i) is methacrylamide, component (ii) is piperazine bisacrylamide, component (iii) is vinyl sulfonic acid, and component (iv) is stearyl methacrylate.

31. A process in accordance with claim 16 further comprising drawing said mixture into a capillary prior to step (b), and in which step (b) is performed inside said capillary.

* * * * *